(12) United States Patent
Almering

(10) Patent No.: US 7,982,086 B2
(45) Date of Patent: Jul. 19, 2011

(54) DEISOBUTENIZER

(75) Inventor: Martinus J. Almering, Pasadena, TX (US)

(73) Assignee: Catalytic Distillation Technologies, Pasadena, TX (US)

(*) Notice: Subject to any disclaimer, the term of this patent is extended or adjusted under 35 U.S.C. 154(b) by 389 days.

(21) Appl. No.: 12/364,961

(22) Filed: Feb. 3, 2009

(65) Prior Publication Data

US 2010/0197987 A1 Aug. 5, 2010

(51) Int. Cl.
*C07C 5/25* (2006.01)

(52) U.S. Cl. ... 585/664; 585/802; 585/809; 203/DIG. 6; 208/347; 208/354; 208/355; 208/358

(58) Field of Classification Search .................. None
See application file for complete search history.

(56) References Cited

U.S. PATENT DOCUMENTS

| | | | |
|---|---|---|---|
| 2,403,672 A * | 7/1946 | Matuszak | 585/664 |
| 3,780,130 A * | 12/1973 | Miller | 285/731 |
| 4,215,011 A | 7/1980 | Smith, Jr. | |
| 4,482,775 A * | 11/1984 | Smith, Jr. | 585/671 |
| 4,718,986 A * | 1/1988 | Comiotto et al. | 203/26 |
| 5,087,780 A * | 2/1992 | Arganbright | 585/259 |
| 5,189,001 A | 2/1993 | Johnson | |
| 5,730,843 A | 3/1998 | Groten et al. | |
| 5,898,091 A | 4/1999 | Chodorge et al. | |
| 5,969,203 A | 10/1999 | Dorbon et al. | |
| 6,000,685 A | 12/1999 | Groten et al. | |
| 6,054,630 A | 4/2000 | Mikitenko et al. | |
| 6,075,173 A | 6/2000 | Chodorge et al. | |
| 6,242,661 B1 | 6/2001 | Podrebarac et al. | |
| 6,271,430 B2 | 8/2001 | Schwab et al. | |
| 6,333,442 B1 | 12/2001 | Cosyns et al. | |
| 6,358,482 B1 | 3/2002 | Chodorge et al. | |
| 6,580,009 B2 | 6/2003 | Schwab et al. | |
| 6,683,019 B2 | 1/2004 | Gartside et al. | |
| 6,727,396 B2 * | 4/2004 | Gartside | 585/324 |
| 6,777,582 B2 | 8/2004 | Gartside et al. | |
| 7,214,841 B2 | 5/2007 | Gartside et al. | |
| 7,223,895 B2 | 5/2007 | Sumner | |
| 2006/0135828 A1 * | 6/2006 | Shutt | 585/250 |

OTHER PUBLICATIONS

International Search Report and Written Opinion issued Jul. 22, 2010 in corresponding International application No. PCT/US2010/020585 (6 pages).

* cited by examiner

*Primary Examiner* — Tam M Nguyen
(74) *Attorney, Agent, or Firm* — Osha • Liang LLP

(57) ABSTRACT

A process for fractionating isobutene from normal butenes, including: introducing hydrogen and a feed stream comprising isobutene, 1-butene, and 2-butene into a first column including a reaction zone containing a hydroisomerization catalyst operating at a first pressure and concurrently: (i) converting at least a portion of the 1-butene to 2-butene, and (ii) separating isobutene from the 2-butene; recovering a first overheads fraction comprising isobutene from the first column; recovering a first bottoms fraction comprising isobutene, 2-butene, and unreacted 1-butene from the first column; introducing the first bottoms fraction into a top portion of a second column comprising a fractionation column operating at a second pressure lower than the first pressure; separating the first bottoms into a second overheads fraction comprising isobutene and 1-butene and a second bottoms fraction comprising 2-butene; compressing the second overheads fraction; and introducing the compressed second overheads fraction to a lower portion of the first column.

20 Claims, 1 Drawing Sheet

DEISOBUTENIZER

BACKGROUND OF DISCLOSURE

1. Field of the Disclosure

Embodiments disclosed herein relate generally to the processing of a $C_4$ hydrocarbon cut from a cracking process, such as steam or fluid catalytic cracking. More specifically, embodiments disclosed herein relate to the separation and recovery of isobutene from a $C_4$ hydrocarbon cut, where the resulting $C_4$ fractions, which may separately include 2-butene, 1-butene, and/or isobutene, may be used in subsequent alkylation, oligomerization, etherification, dehydrogenation, and metathesis processes.

2. Background

In typical olefin plants, such as illustrated in U.S. Pat. No. 7,223,895, there is a front-end demethanizer for the removal of methane and hydrogen followed by a deethanizer for the removal of ethane, ethylene and $C_2$ acetylene. The bottoms from this deethanizer tower consist of a mixture of compounds ranging in carbon number from $C_3$ to $C_6$. This mixture may be separated into different carbon numbers, typically by fractionation.

The $C_3$ cut, primarily propylene, is removed as product and is ultimately used for the production of polypropylene or for chemical synthesis such as propylene oxide, cumene, or acrylonitrile. The methyl acetylene and propadiene (MAPD) impurities must be removed either by fractionation or hydrogenation. Hydrogenation is preferred since some of these highly unsaturated $C_3$ compounds end up as propylene thereby increasing the yield.

The $C_4$ cut consisting of $C_4$ acetylenes, butadienes, iso- and normal butenes, and iso- and normal butane can be processed in many ways. A typical steam cracker $C_4$ cut contains the following components in weight %:

TABLE 1

Typical $C_4$ cut components and weight percentages.

| | |
|---|---|
| $C_4$ Acetylenes | Trace |
| Butadienes | 33% |
| 1-butene | 15% |
| 2-butene | 9% |
| Isobutene | 30% |
| Iso- and Normal Butanes | 13% |

Typically, the butadiene and $C_4$ acetylenes are removed first. This can be accomplished by either hydrogenation or extraction. If extraction is employed, the remaining 1-butene and 2-butene remain essentially in the same ratio as that of the initial feedstock. If hydrogenation is employed, the initial product from butadiene hydrogenation is 1-butene. Subsequently, hydroisomerization occurs within the same reaction system converting the 1-butene to 2-butene. The extent of this reaction depends upon catalyst and reaction conditions within the hydrogenation system. However, it is common practice to limit the extent of hydroisomerization in order to avoid "over hydrogenation" and the production of butanes from butenes. This would represent a loss of butene feedstock for downstream operations. The butenes remaining in the mixture consist of normal olefins (1-butene, 2-butene) and iso-olefin (isobutene). The balance of the mixture consists of both iso- and normal-butanes from the original feed plus what was produced in the hydrogenation steps and any small quantity of unconverted or unrecovered butadiene.

The butenes have many uses. One such use is for the production of propylene via metathesis. Another is for the production of ethylene and hexene via metathesis. Conventional metathesis involves the reaction of normal butenes (both 1-butene and 2-butene) with ethylene. These reactions occur in the presence of a group VIA or VIIA metal oxide catalyst, either supported or unsupported. Various metathesis processes are disclosed in, for example, U.S. Pat. Nos. 6,683,019, 6,580,009, 6,271,430, 6,777,582, and 6,727,396.

In some cases, an isobutene removal step is employed prior to metathesis. Options include reacting it with methanol to produce methyl tertiary butyl ether (MTBE) or separating the isobutene from the butenes by fractionation. U.S. Pat. No. 6,358,482 discloses the removal of isobutene from the $C_4$ mixture prior to metathesis. This scheme is further reflected in U.S. Pat. Nos. 6,075,173 and 5,898,091.

Isobutene removal from the $C_4$ stream can also be accomplished by employing a combined catalytic distillation hydroisomerization deisobutenizer system to both remove the isobutene and recover n-butenes at high efficiency by isomerizing the 1-butene to 2-butene with known isomerization catalysts, thus increasing the volatility difference. This technology combines conventional fractionation for isobutene removal with hydroisomerization within a catalytic distillation tower. In U.S. Pat. No. 5,087,780 to Arganbright, 2-butene is hydroisomerized to 1-butene as the fractionation occurs. This allows greater than equilibrium amounts of 1-butene to be formed as the mixture is separated. Similarly, 1-butene can be hydroisomerized to 2-butene in a catalytic distillation tower. In separating a $C_4$ stream containing isobutene, 1-butene, and 2-butene (plus paraffins), it is difficult to separate isobutene from 1-butene since their boiling points are very close. By employing simultaneous hydroisomerization of the 1-butene to 2-butene with fractionation of isobutene, isobutene can be separated from the normal butenes at high efficiency.

In U.S. Pat. No. 7,214,841, for example, the $C_4$ cut from a hydrocarbon cracking process is first subjected to auto-metathesis prior to any isobutene removal and without any ethylene addition, favoring the reactions which produce propylene and pentenes. The ethylene and propylene produced are then removed leaving a stream of the C.sub.4's and heavier components. The $C_5$ and heavier components are then removed leaving a mixture of 1-butene, 2-butene, isobutene, and iso- and normal butanes. The isobutene is next removed preferably by a catalytic distillation hydroisomerization deisobutenizer. The isobutene-free $C_4$ stream is then mixed with the product ethylene removed from the auto-metathesis product together with any fresh external ethylene needed and subjected to conventional metathesis producing additional propylene.

In the above processes, separation of isobutene from normal butenes may be accomplished via isomerization of 1-butene to 2-butene, facilitating the fractionation of the normal butene from isobutene. The continuous fractionation of 2-butenes away from the reaction zone improves the driving force of the isomerization to 2-butenes. The resulting products can achieve conversion beyond the equilibrium ratio of the reaction. Unfortunately, due to high reflux requirements, these processes use large amounts of utilities, such as cooling water and steam.

Accordingly, there exists a significant need for $C_4$ separation processes that may provide the desired separations at reduced capital cost and/or utility consumptions.

SUMMARY OF THE DISCLOSURE

In one aspect, embodiments disclosed herein relate to a process for fractionating isobutene from normal butenes, including: introducing hydrogen and a feed stream comprising isobutene, 1-butene, and 2-butene into a first column comprising a catalytic distillation reactor system containing at least one reaction zone comprising a hydroisomerization catalyst operating at a first pressure and concurrently (i) converting at least a portion of the 1-butene to 2-butene and (ii) separating isobutene from the 2-butene via fractional distillation; recovering a first overheads fraction comprising isobutene from the first column; recovering a first bottoms fraction comprising isobutene, 2-butene, and any unreacted 1-butene from the first column; introducing the first bottoms fraction into a top portion of a second column comprising a fractionation column operating at a second pressure lower than the first pressure; separating the first bottoms into a second overheads fraction comprising isobutene and 1-butene and a second bottoms fraction comprising 2-butene; and compressing the second overheads fraction and introducing the compressed second overheads fraction to a lower portion of the first column.

In another aspect, embodiments disclosed herein relate to a process for fractionating a mixed-$C_4$ hydrocarbon stream, including: introducing hydrogen and a mixed-$C_4$ stream comprising n-butenes, isobutene, and paraffins into a first column comprising a catalytic distillation reactor system containing at least one reaction zone comprising a hydroisomerization catalyst operating at a first pressure and concurrently (i) converting at least a portion of the 1-butene to 2-butene, and (ii) separating isobutene from the 2-butene via fractional distillation; recovering a first overheads fraction comprising isobutene from the first column; recovering a first bottoms fraction comprising isobutene, 2-butene, and any unreacted 1-butene from the first column; introducing the first bottoms fraction into a top portion of a second column comprising a fractionation column operating at a second pressure lower than the first pressure; separating the first bottoms into a second overheads fraction comprising isobutene and 1-butene and a second bottoms fraction comprising 2-butene; and compressing the second overheads fraction and introducing the compressed second overheads fraction to a lower portion of the first column.

Other aspects and advantages will be apparent from the following description and the appended claims.

DETAILED DESCRIPTION

Figure 1:
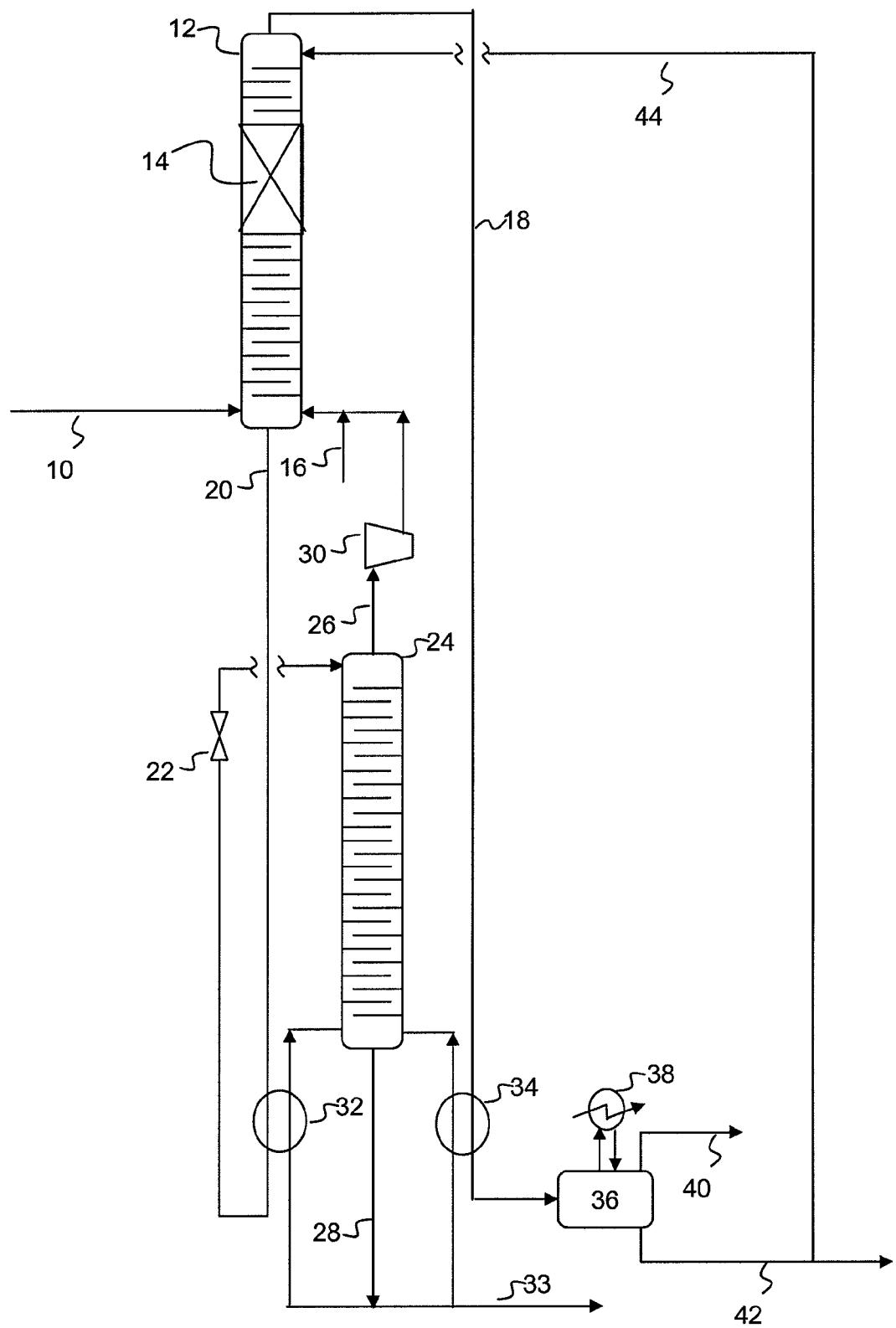
FIG. 1 is a simplified process flow diagram of a process for separating isobutene and normal butenes according to embodiments disclosed herein.

Embodiments disclosed herein relate generally to the processing of a $C_4$ hydrocarbon cut from a cracking process, such as steam or fluid catalytic cracking. More specifically, embodiments disclosed herein relate to the separation and recovery of isobutene from a $C_4$ hydrocarbon cut, where the resulting $C_4$ fractions, which may separately include 2-butene, 1-butene, and/or isobutene, may be used in subsequent alkylation, oligomerization, etherification, dehydrogenation, and metathesis processes.

The mixed $C_4$ feed to processes disclosed herein may include $C_3$ to $C_{6+}$ hydrocarbons, including $C_4$, $C_4$ to $C_5$, and $C_4$ to $C_6$ cracker effluents, such as from a steam cracker or a fluid catalytic cracking (FCC) unit. Other refinery hydrocarbon streams containing a mixture of $C_4$ olefins may also be used. When $C_3$, $C_5$ and/or $C_6$ components are present in the feed, the stream may be pre-fractionated to result in a primary $C_4$ cut, a $C_4$ to $C_5$ cut, or a $C_4$ to $C_6$ cut.

$C_4$ components contained in the feed stream may include n-butane, isobutane, isobutene, 1-butene, 2-butene, and butadiene. In some embodiments, the mixed $C_4$ feed may be pretreated to remove diolefins and acetylenes. For example, when butadiene is present in the $C_4$ feed, the butadiene may be removed via hydrogenation or extraction.

The mixed $C_4$ feed following or in conjunction with butadiene hydrogenation may be fed to an integrated two-column system for the isomerization of 1-butene to 2-butene and the separation of isobutene from the 2-butene. The first column, a catalytic distillation reactor system, may include one or more fractionation zones and at least one reaction zone containing a hydroisomerization catalyst. Concurrently in the first column, at least a portion of the 1-butene may be converted to 2-butene, facilitating the separation of isobutene, which may be recovered as an overheads fraction along with hydrogen fed to the reactor for the hydroisomerization reaction. Isobutene, any unreacted 1-butene, and 2-butene may be recovered as a bottoms fraction from the first column.

The catalyst in the hydroisomerization reaction zone may include catalysts comprising one or more metals, for example from group 10 of the periodic classification (Ni, Pd, Pt), deposited on a support. Catalyst comprising at least one palladium compound fixed on a refractory mineral support, for example alumina are used in some embodiments. The amount of palladium on the support can be in the range 0.01% to 5% by weight, such as in the range 0.05% to 1% by weight.

The catalyst in the hydroisomerization reaction zone may be bulk-loaded, made up of extrudates, pellets, balls, open ring-shapes, etc. In some embodiments, the catalyst is part of a structure, such as catalyst deposited on the surface of wire mesh or other types of gauzes or catalyst contained on the walls of a monolith structure. For example, the catalyst may be contained in specially-designed containers, as described in U.S. Pat. Nos. 6,000,685, 5,730,843, 5,189,001, and 4,215,011.

The first column may operate at a pressure of at least 5 bar. For example, in some embodiments the first column may operate at a pressure in the range from about 5 bar to about 15 bar; in the range from about 5.5 bar to about 10 bar in other embodiments; and from about 7 bar to about 9 bar in yet other embodiments. The first column may operate at temperatures such that the reaction temperature (temperature within the hydroisomerization reaction zone) is within the range from about 45° C. to about 100° C.; within the range from about 50° C. to about 70° C. in other embodiments; and from about 55° C. to about 65° C. in yet other embodiments.

The bottoms fraction recovered from the first column may be fed to an upper portion of a second column as the sole feed or as reflux. The second column contains mass transfer contacting devices (trays, packing, etc.) to separate the isobutene from 2-butene. The isobutene may be recovered as an overheads fraction, and the 2-butene may be recovered as a bottoms fraction. Overheads recovered from the second column, which may including isobutene, 1-butene, and 2-butene may be fed to a bottom portion of the first column, thus integrating the two columns.

In some embodiments, the isobutene content, based on a combined amount of $C_4$ olefins in the second column bottoms fraction; may be less than 5%; less than 3% in other embodiments; less than 2% in other embodiments; less than 1% in other embodiments; and less than 0.5% in yet other embodiments.

The second column may be operated at a lower pressure than the first column. If necessary, the overheads fraction from the second column may be compressed to a pressure sufficient to cause flow of the overheads fraction from the second column into the bottom portion of the first column.

The second column may operate at a pressure of less than 5 bar. For example, in some embodiments the second column may operate at a pressure in the range from about 0.5 bar to about 5 bar; in the range from about 1.5 bar to about 4.5 bar in other embodiments; and from about 2.5 bar to about 4 bar in yet other embodiments.

Operating the second column at a lower pressure allows for more efficient separation of the isobutene from the 2-butene, thus reducing reflux requirements for the integrated columns. Decreased reflux requirements may allow for the overall size of the columns to be reduced as compared to a single column for the concurrent hydroisomerization and fractionation of isobutene from normal butenes, at a given throughput and fractionation specification (such as bottoms product isobutene specifications).

In addition to reducing reflux requirements, the dual pressure integrated column may also allow for a significant reduction in utilities, such as cooling water and or steam requirements. For example, the second column may operate at temperatures less than the first column overheads temperature, allowing for heat integration. The second column may operate at temperatures within the range from about 20° C. to about 50° C. in some embodiments; within the range from about 25° C. to about 50° C. in other embodiments; and from about 30° C. to about 50° C. in yet other embodiments. Additionally, compression of the second column overheads fraction may supply heat for maintaining a desired bottoms temperature in the first column.

Heat recovered the first column bottoms fraction and/or overheads fraction may allow for significant decreases in both heating and cooling utility consumption. It is noted, however, that some utilities will be required for column start-up. As compared to a single column (i.e., single pressure) designed for a similar capacity, embodiments of the integrated columns for the separation of isobutene from normal butenes disclosed herein may reduce steam or other heating fluid requirements by up to 100%; by at least 50% in some embodiments; by at least 75% in other embodiments; by at least 90% in other embodiments; and by at least 95% in yet other embodiments. Additionally, as compared to a single column (i.e., single pressure) designed for a similar capacity, embodiments of the integrated columns for the separation of isobutene from normal butenes disclosed herein may reduce cooling water or cooling fluid requirements by up to 90%; by at least 50% in some embodiments; by at least 60% in other embodiments; by at least 70% in other embodiments; and by at least 75% in yet other embodiments.

One example of a heat integrated isobutene separation system according to embodiments disclosed herein is illustrated in FIG. 1, which is a simplified process flow diagram of a process for separating isobutene from normal butenes according to embodiments disclosed herein is illustrated. A mixed $C_4$ stream containing n-butenes, isobutene, and paraffins may be fed via flow line 10 to a first column 12, which may be a catalytic distillation reactor system including at least one reaction zone 14 containing a hydroisomerization catalyst. To aid in the hydroisomerization, hydrogen may be fed to first column 12 via flow line 16.

In first column 12, 1-butene and hydrogen are contacted with the hydroisomerization catalyst to convert at least a portion of the 1-butene to 2-butene. Concurrently, the isobutene and resulting 2-butene are separated via fractional distillation. Hydrogen and isobutene may be recovered from first column 12 as a first overheads fraction 18. Isobutene, 2-butene, and any unreacted 1-butene, may be recovered from first column 12 as a first bottoms fraction 20.

First bottoms fraction 20 may be flashed across valve 22, to reduce the pressure of the stream, and fed to an upper portion of second column 24. Second column 24, operating at a lower pressure than first column 12, may separate 1-butene and isobutene, recovered as a second overheads fraction 26, from 2-butene, which may be recovered as a second bottoms fraction 28. A portion of second bottoms fraction 28 may be fed to reboilers 32, 34, and a portion may be recovered as a hydrocarbon stream having a reduced isobutene content via flow line 33.

Second overheads fraction 26 may be compressed via compressor 30, increasing the pressure of second overheads fraction 26 to allow flow into a lower portion of high pressure first column 12. Compressor 30 may also increase the temperature of second overheads fraction, in some embodiments providing sufficient heat, along with any feed preheaters used for feed stream 10, to provide for vapor traffic within first column 12.

Reboil vapor to second column 24 may be provided via indirect heat exchange with at least one of first bottoms fraction 20 and first overheads fraction 18. For example, at least a portion of second bottoms fraction 28 may be heated via indirect heat exchange with first bottoms fraction 20 in reboiler 32.

As another example, a portion of second bottoms fraction 28 may be heated via indirect heat exchange with first overheads fraction 18 in reboiler 34. Reboiler 34 may be directly coupled to a condenser/accumulator 36. At least a portion of first overheads fraction 18 may condense due to indirect heat exchange with bottoms fraction 28. If necessary, additional hydrocarbons may be condensed via indirect heat exchange with a supplemental heat exchanger 38.

Hydrogen may be recovered from condenser/accumulator 36 via flow line 40. A liquid fraction including isobutene may be recovered from condenser/accumulator 36 via flow line 42, a portion of which may be fed as reflux to first column 12 via flow line 44.

Isobutene and normal butene streams recovered via processes disclosed herein may be fed to one or more downstream processes. For example, isobutene streams may be fed to one or more of an auto-metathesis process, an oligomerization process, an etherification process, or an alkylation process; normal butenes may be fed to auto-metathesis, conventional metathesis, dehydrogenation, and other various processes for converting $C_4$ olefins to valued end products, including light olefins (ethylene and propylene), butadiene, gasoline, and other chemicals as known in the art.

EXAMPLES

The following examples are derived from modeling techniques. Although the work has been performed, the Inventors do not present these examples in the past tense to comply with applicable rules.

Example 1

A $C_4$ hydrocarbon feed is treated according to the process as illustrated and described with respect to FIG. 1. The $C_4$ feed (stream 10) and hydrogen (stream 16) are introduced to a bottom portion of a first distillation column 12 including a hydroisomerization reaction zone 14. Following the concurrent reaction and separation according to embodiments disclosed herein, a top fraction (stream 42), a bottom fraction (stream 33), and a vent (stream 40) are each recovered from the system, with the resulting compositions and flow rates as shown in Table 2.

TABLE 2

| | Stream #: | | | | |
|---|---|---|---|---|---|
| | 10 | 16 | 40 | 42 | 33 |
| | Stream Description | | | | |
| Composition | C4 Feed wt % | H2 Feed wt % | Vent wt % | Tops wt % | Bottoms wt % |
| H2 | | 100.0 | 1.6 | | |
| C3s | 0.1 | | 0.7 | 0.2 | |
| i-Butane | 30.9 | | 58.7 | 55.3 | 0.0 |
| i-Butene | 23.8 | | 36.5 | 41.2 | 2.0 |
| n-Butane | 9.5 | | 0.2 | 0.4 | 21.5 |
| 1-Butene | 8.7 | | 1.6 | 1.9 | 1.2 |
| t-2-Butene | 15.9 | | 0.6 | 0.9 | 43.1 |
| c-2-Butene | 10.2 | | 0.1 | 0.1 | 30.1 |
| n-C5 | 0.9 | | 0.0 | 0.0 | 2.1 |
| Total, kg/h | 51453 | 10 | 419 | 28318 | 22726 |

The simulation results were also used to estimate utility consumption and column size as compared to a two-column, non-integrated system operating without a pressure differential. The column size and utilities for the systems are compared in Table 3, the simulation results indicating that a decrease in second column size (such as internal diameter) may be attained and that the per year utility consumption may be decreased by an estimated 40%, as based on operating for 8000 hours per year.

TABLE 3

| | | Comparative 2-column system | Example 1 |
|---|---|---|---|
| Major Equipment | | | |
| Column 1: | ID, m | 4.7 | 4.7 |
| | T/T, m | 39 | 39 |
| Column 2: | ID, m | 4.7 | 4.4 |
| | T/T, m | 38 | 38 |
| Compressor | MW | | 4 |
| Utility Consumption | | | |
| LP Steam | t/h | 44.8 | |
| Cooling Water | m3/h (d = 10° C.) | 2200 | 250 |
| Electricity | kW | 100 | 4070 |
| Utility Consumption, $ | | | |
| LP Steam | 10 US$/t | $3,584,724 | 0 |
| Cooling Water | 0.01 $/m3 | $ 176,000 | $ 20,000 |
| Electricity | 0.07 $/kWh | $ 56,000 | $2,279,200 |
| Total Utility Cost | $/year | $3,816,724 | $2,299,200 |

As described above, embodiments disclosed herein provide for efficient separation of isobutene from normal butenes. Advantageously, embodiments disclosed herein may reduce utility consumption through use of an integrated heat pump system, reducing as much as 100% of the steam requirements and up to about 75% or more of cooling water requirements. Although the electricity consumption is substantially increased to power the compressor, overall utility costs are reduced by 40%. Additionally, the integrated column may require significantly less reflux (liquid traffic), thus allowing for a reduction in second column size as compared to a single pressure column(s) system for a given throughput and fractionation specification.

Additionally, systems currently used for the isomerization of 1-butene to 2-butene and separation of isobutene therefrom may include two existing columns. Such two column systems may be converted to integrated columns as described herein with minimal change to the existing columns.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for fractionating isobutene from normal butenes, comprising:
   introducing hydrogen and a feed stream comprising isobutene, 1-butene, and 2-butene into a first column comprising a catalytic distillation reactor system containing at least one reaction zone comprising a hydroisomerization catalyst operating at a first pressure and concurrently:
      (i) converting at least a portion of the 1-butene to 2-butene;
      (ii) separating isobutene from the 2-butene via fractional distillation;
   recovering a first overheads fraction comprising isobutene from the first column;
   recovering a first bottoms fraction comprising isobutene, 2-butene, and any unreacted 1-butene from the first column;
   introducing the first bottoms fraction into a top portion of a second column comprising a fractionation column operating at a second pressure lower than the first pressure;
   separating the first bottoms into a second overheads fraction comprising isobutene and 1-butene and a second bottoms fraction comprising 2-butene; and
   compressing the second overheads fraction and introducing the compressed second overheads fraction to a lower portion of the first column.

2. The process of claim 1, further comprising generating reboil vapor for the second column by heating at least a portion of the second bottoms fraction via indirect heat exchange with at least one of the first bottoms fraction and the first overheads fraction.

3. The process of claim 2, wherein the indirect heat exchange with the first overheads fraction condenses at least a portion of the first overheads fraction.

4. The process of claim 3, further comprising returning at least a portion of the condensed first overheads fraction to the first column as reflux.

5. The process of claim 3, further comprising condensing at least a portion of the first overheads fraction via indirect heat exchange with at least one of cooling water, a cooling gas, or a refrigerant.

6. The process of claim 1, wherein the first column is operated at a pressure in the range from greater than about 5 bar.

7. The process of claim 6, wherein the first column is operated at a pressure in the range from about 5.5 bar to about 10 bar.

8. The process of claim 6, wherein the second column is operated at a pressure less than about 5 bar.

9. The process of claim 8, wherein the second column is operated at a pressure in the range from about 2 bar to about 4.5 bar.

10. The process of claim 1, wherein the second bottoms fraction comprises less than 3 weight percent isobutene, based on a total amount of isobutene, 1-butene, and 2-butene.

11. A process for fractionating a mixed-$C_4$ hydrocarbon stream, comprising:

introducing hydrogen and a mixed-$C_4$ stream comprising n-butenes, isobutene, and paraffins into a first column comprising a catalytic distillation reactor system containing at least one reaction zone comprising a hydroisomerization catalyst operating at a first pressure and concurrently:
  (i) converting at least a portion of the 1-butene to 2-butene;
  (ii) separating isobutene from the 2-butene via fractional distillation;
recovering a first overheads fraction comprising isobutene from the first column;
recovering a first bottoms fraction comprising isobutene, 2-butene, and any unreacted 1-butene from the first column;
introducing the first bottoms fraction into a top portion of a second column comprising a fractionation column operating at a second pressure lower than the first pressure;
separating the first bottoms into a second overheads fraction comprising isobutene and 1-butene and a second bottoms fraction comprising 2-butene; and
compressing the second overheads fraction and introducing the compressed second overheads fraction to a lower portion of the first column.

12. The process of claim 11, further comprising generating reboil vapor for the second column by heating at least a portion of the second bottoms fraction via indirect heat exchange with at least one of the first bottoms fraction and the first overheads fraction.

13. The process of claim 12, wherein the indirect heat exchange with the first overheads fraction condenses at least a portion of the first overheads fraction.

14. The process of claim 13, further comprising returning at least a portion of the condensed first overheads fraction to the first column as reflux.

15. The process of claim 13, further comprising condensing at least a portion of the first overheads fraction via indirect heat exchange with at least one of cooling water, a cooling gas, or a refrigerant.

16. The process of claim 11, wherein the first column is operated at a pressure in the range from greater than about 5 bar.

17. The process of claim 16, wherein the first column is operated at a pressure in the range from about 5.5 bar to about 10 bar.

18. The process of claim 16, wherein the second column is operated at a pressure less than about 5 bar.

19. The process of claim 18, wherein the second column is operated at a pressure in the range from about 2 bar to about 4.5 bar.

20. The process of claim 11, wherein the second bottoms fraction comprises less than 3 weight percent isobutene, based on a total amount of isobutene, 1-butene, and 2-butene.

\* \* \* \* \*